United States Patent
Tsou et al.

(10) Patent No.: US 6,278,010 B1
(45) Date of Patent: Aug. 21, 2001

(54) PROCESS FOR PRODUCING MODIFIED ZINC ACRYLATE FINE POWDER

(75) Inventors: Chiu-Peng Tsou; Ruey-Tsan Chen; Chang-Min Su, all of Ping-Chen (TW)

(73) Assignee: Kuo Ching Chemical Co., Ltd., Taoyuan County (TW)

( * ) Notice: Subject to any disclaimer, the term of this patent is extended or adjusted under 35 U.S.C. 154(b) by 0 days.

(21) Appl. No.: 09/725,099

(22) Filed: Nov. 29, 2000

(51) Int. Cl.$^7$ ....................................................... C07F 3/06
(52) U.S. Cl. ................................................................ 556/131
(58) Field of Search ............................................. 556/131

(56) References Cited

U.S. PATENT DOCUMENTS 5,789,616 * 8/1998 Kobayashi et al. .................. 562/598

* cited by examiner

Primary Examiner—Porfirio Nazario-Gonzalez
(74) Attorney, Agent, or Firm—Dougherty & Troxell

(57) ABSTRACT

An improved process for producing modified zinc acrylate fine powder is disclosed, comprising adding acrylic acid in a organic liquid medium and reacting in the presence of zinc oxide and fatty acid, and after completing of the reaction, adding nonionic surfactant, blending homogeneously, removing said organic medium and water by distillation under reduced pressure and simple pulverizing. The process can attains uniform diffusion in a state very rarely inducing fast adhesion or formation of cluster in the drying step, and, permits easy pulverization into a fine powder, 99% of which has a particle size<44 $\mu$m and thereby can be used directly without needing any sieving.

4 Claims, No Drawings

PROCESS FOR PRODUCING MODIFIED ZINC ACRYLATE FINE POWDER

The invention relates to an improved process for producing modified zinc acrylate fine powder by reacting acrylic acid in the presence of zinc oxide, fatty acid and a liquid medium and thereafter, blending homogeneously with a nonionic surfactant, drying and pulverization.

BACKGROUND OF THE INVENTION

Zinc acrylate is a known chemical used as a cross-linking agent for incorporating into a rubber composition to cross-link adjacent chains of rubber molecules. After cross-linking, the physical property of the rubber, such as elasticity; tensile strength and the like, is determined by the cross-linking density of a given chain length and the number of zinc ion. U.S. Pat. No. 4,561,657 disclosed a process for producing a golf ball, comprising of coating zinc acrylate powder with fatty acid or zinc salt thereof, and then incorporating the resulting powder in the rubber composition as a cross-linking agent for the production of a solid golf ball that has enhanced impact resilience, hardness and weight uniformity. Accordingly, modified zinc acrylate powder has a practical utility in the industry.

A modified zinc acrylate refers to a powder produced by coating a fatty acid or zinc salt thereof on the zinc acrylate powder in the course of its producing. Producing of zinc acrylate by reacting zinc oxide with acrylic acid is a known process per se. Nevertheless, to produce a modified zinc acrylate powder having a specific property by adjusting the formulation and/or by changing the way of adding raw materials in the course of production comprises a specific technique. Different producing process may affect the physicochemical properties such as, particle size, zinc content and acrylate content, of the resulted modified zinc acrylate powder as well as can influence the end use of such a chemical. Various prior techniques in connection with the producing of zinc acrylate powder have been proposed, such as those described in JP-A-52-154,436, JP-A-53-83,834, JP-A-60-94,434, and JP-A-02-218,639. However, there were disadvantages associated with these prior art techniques, such as, lacking an efficient drying process for removing water and organic liquid medium, time-consumption in filtration or distillation under reduced pressure, trouble in adhering stirring blades or the wall of the reactor that might result in the loss of the product and the laborsome cleansing of the reactor, or aggregation of the crude product. With respect to the aggregated product, an additional equipment is needed for grinding and sieving such that the product can pass a specified particle size of 325 mesh (<44 µm).

U.S. Pat. No. 5,789,616 disclosed a process comprising adding at the first an anionic surfactant, sodium dioctyl sulfosuccinate, in toluene, following with adding successively zinc oxide, fatty acid and acrylic acid, and, after completion of the reaction, drying by distillation at a reduced pressure, and pulverizing and sieving the thus produced crude product to yield a modified zinc acrylate powder having a particle size characterized in that 64% of particles<44 µm, 54% of particles<10 µm, and 41% of particles<5 µm, while the part that had a particle size of>105 µm and must be removed by sieving was estimated to be 31%. The anionic surfactant, i.e. sodium dicotyl sulfosuccinate, used in this technique to be added at the first stage of the reaction might cause the swelling of the content in the reaction mixture such that in the subsequent addition of acrylic acid, might lead to local thickening and hence difficulty for stirring, and therefore, the reaction could be completely only through slow addition of raw material and postponing the reaction time. This might be the cause that made the zinc acrylate powder thus produced coarser and the particle size distributions non-uniform. On the other hand, it had an advantage that the trouble of sticking the wall of the reactor and the drying tank in the course of drying could be avoided.

SUMMARY OF THE INVENTION

The main object of the invention aims to solve the above-mentioned disadvantages associated with the prior art, and to provide an improved process of economic efficiency for producing a modified zinc acrylate fine powder having a uniform particle size distribution and a particle size of less than 44 µm.

Accordingly, the invention provides an improved process for producing modified zinc acrylate fine powder, comprising adding acrylate acid in organic liquid medium and reacting in the presence of zinc oxide and fatty acid, and after completing of the reaction, adding 0.02 to 1.0 wt. % of nonionic surfactant, and in particular, polyoxyethylene alkyl ether having HLB ion the range 8 to 17, blending homogeneously, drying by distillation under reduced pressure and pulverizing. A modified zinc acrylate fine powder having a particle size of<44 µm can be obtained directly and no sticking on the stirring blade and the wall of the reactor occurs.

DETAILED DESCRIPTION OF THE INVENTION

As stated above, the invention provides an improved process for producing zinc acrylate fine powder, comprising the steps of:

1. Stirring under heating zinc oxide and fatty acid in a liquid medium, adding acrylic acid at controlled temperature, and continuing heating till a constant pH of the solution;

2. Adding 0.02 to 1.0% by weight of a nonionic surfactant in the reaction mixture containing zinc acrylate in step 1 and stirring to form a homogeneous cream; and 3. Removing organic liquid medium and water by distillation under reduced pressure, and pulverizing to afford directly a zinc acrylate fine powder.

In the process for producing zinc acrylate fine powder according to the invention, the ratio among amounts of zinc oxide, fatty acid, acrylic acid and the organic liquid medium used may have an effect on the particle size, the zinc content and the content of acryl group of the modified zinc acrylate powder thus produced. Therefore, the mole ratio of zinc oxide, fatty acid and acrylic acid used in the process of the invention is suitably controlled in the range of 0.50–0.55/ 0.02–0.04/1.00, while the amount of the organic liquid medium should be more than 0.8 times, preferably 1 to 4 times of the total amount of reactants.

Zinc oxide used in the process according to the invention is preferably a powder. Fatty acid used in the process of the invention is selected from palmitic acid and stearic acid. The liquid medium that can be used in the invention is selected from C6 to C10 aromatic hydrocarbon, and may be benzene, toluene, or xylene. The liquid medium may contain 0.5 to 10% of water.

The temperature in the course of adding material and reaction may be in the range of 40 to 75° C., preferably in the range of 45 to 65° C.

The nonionic surfactant useful in the invention is selected from one or more polyoxyethylene alkyl ether. Among the commercial available polyoxyethylene alkyl ethers, those having a hydrophilic-lipophilic balance (HLB) value in the range of 8 to 17 can give better effect, and examples thereof are those sold under trade names as Sinopol 1830 (HLB 16.6), Sinopol 1807 (HLB 10.7), Sinopol 1536 (HLB 12.8), Sinopol 1307 (HLB 12.7), Sinopol 1100H (HLB 12.7).

The modified zinc acrylate fine powder produced by the process according to the invention is a zinc acrylate mixture comprising zinc acrylate powder coated with a fatty acid or salt thereof, and is characterized in that it has a content of zinc acrylate of 90±5 wt %, an as content of 35 to 40 wt %, and an acryl content of 50 to 58 wt %. The characteristics of particle size of the modified zinc acrylate fine powder produced according to the process of the invention exhibits as, by way of an example, that analyzed for the powder obtained in Example 1: 99+% of particles<44 $\mu$m, 26.15% of particles<10 $\mu$m and 9.55% of particles<5 $\mu$m, such that the as-produced powder need not sieving and can meet the requirement of the market in terms of the fineness and uniformity.

The technical feature of the process according to the invention comprises taking advantage of the characteristics of the zinc salt of fatty acid as a good dispersant for a powder, thereby, renders stirring of the reaction mixture in the course of adding acrylic acid more easy and thus a uniform reaction. In comparison with prior art technique, this can reduce considerably time for the addition of reactants and for completion of reaction, and further, the zinc acrylate powder thus produces is more uniform. In other words, according to the invention, the selection of the nonionic surfactant having the above-specified HLB value and addition of it into the zinc acrylate reaction product can facilitate uniform dispersion of the powder, water and the organic liquid medium, improve the efficiency for removing organic liquid medium and water through distillation under reduced pressure in the course of drying, as well as can avoid the powder from sticking on the stirring blade and the wall of the reactor during operation. Since zinc acrylate fine powder produced according to the invention has 99% of its particles a particle size of<44 $\mu$m, it is superior than those produced by any prior art technique in that it can be used without needing any sieving.

EXAMPLE 1

To a 4000 liter jacketed stainless steel reactor, at room temperature, were fed toluene (1591 kg, moisture content of 3.7%), zinc oxide (403.0 kg, 94.5% purity, 4.68 kmol) and stearic acid (65.7 kg, 0.23 kmol). Then, the temperature was raised to 48±5° C. To the reactor was added dropwise acrylic acid (631 kg, 8.76 kmol) over 2.5 hours, and continued the stirring while keeping at this temperature for additional 2 hours in order to complete the reaction. The pH value of this solution is about 5. To this reaction mixture was added Sinopol 1536 (2.0 kg, HLB 12.8, comprising mainly polyoxyethylene octadecyl ether). After stirring for additional 30 minutes, the resulting cream-like mixture was fed into a paddle dryer for distilling off toluene and water under reduced pressure, and pulverizing the powder. A modified zinc acrylate as a white fine powder was thus obtained (947.8 kg, 94.6% yield). Moisture content<0.5 wt %, acryl content is 52 wt % and ash content is 36.3 wt %, IR spectrum (KBr): $\lambda$ 2917, 2848, 1651, 1603, 1537, 1443, 1372, 1276, 1069, 983 cm$^{-1}$. 99% of its particles have a particle size of<44 $\mu$m as shown in the following data determined by a particle size analyzer (model FRITSCH PARTICLE SIZER ANALYSETTE 22) over the range of 0.31 $\mu$m to 44.85 $\mu$m:

| 1.39% | <1.00 $\mu$m | 4.05% | <2.00 $\mu$m |
|---|---|---|---|
| 6.71% | <3.00 $\mu$m | 9.60% | <4.00 $\mu$m |
| 12.84% | <5.00 $\mu$m | 16.60% | <6.00 $\mu$m |
| 20.96% | <7.00 $\mu$m | 25.88% | <8.00 $\mu$m |
| 31.29% | <9.00 $\mu$m | 37.20% | <10.00 $\mu$m |
| 85.86% | <20.00 $\mu$m | 96.85% | <30.00 $\mu$m |
| 99.13% | <40.00 $\mu$m | | |

After discharging the material, no cluster stuck on the blade in the dryer was observed, and no cake was detected in the powder.

EXAMPLE 2

To a 4000 liter jacketed stainless steel reactor, at room temperature, were fed successively toluene (1472 kg), zinc oxide (366 kg, 99% purity, 4.41 kmol) and stearic acid (65.1 kg, 0.23 kmol). Then, the temperature was raised to 55±5° C. To the reactor was added dropwise acrylic acid (587 kg, 8.15 kmol) over 2.5 hours, and continued the stirring while keeping at this temperature for additional 2 hours in order to complete the reaction. To this reaction mixture was added Sinopol 1807 (2.0 kg, HLB 10.7, comprising mainly polyoxyethylene octadecyl ether). After stirring for additional 30 minutes, the resulting cream-like mixture was fed into a paddle dryer for distilling off toluene and water under reduced pressure, and pulverizing the powder. A modified zinc acrylate as a white fine powder was thus obtained (910 kg, 96.5% yield). Moisture content<0.5 wt %, acryl content is 55 wt % and ash content is 39 wt %. IR spectrum (KBr): $\lambda$ 2917, 2848, 1644, 1576, 1522, 1447, 1433, 1373, 1274, 1067, 974 cm$^{-1}$. After discharging the material, no cluster stuck on the blade in the dryer was observed, and no cake was detected in the powder.

EXAMPLE 3

To a 4000 liter jacketed stainless steel reactor, at room temperature, were fed successively toluene (1472 kg), zinc oxide (310 kg, 99% purity, 3.77 kmol) and stearic acid (56.0 kg, 0.197 kmol). Then, the temperature was raised to 55±5° C. To the reactor was added dropwise acrylic acid (506 kg, 7.02 kmol) over 2.5 hours, and continued the stirring while keeping at this temperature for additional 2 hours in order to complete the reaction. To this reaction mixture was added Sinopol 1536 (2.0 kg, HLB 12.8, comprising mainly polyoxyethylene alkyl ether). After stirring for additional 30 minutes, the resulting cream-like mixture was fed into a paddle dryer for distilling off toluene and water under reduced pressure, and pulverizing the powder. A modified zinc acrylate as a white fine powder was thus obtained (780 kg, 96.7% yield). Moisture content is<0.5 wt %, acryl content is 56.1 wt % and an analyzed ash content is 38 wt %. IR spectrum (KBr): $\lambda$ 2917, 2848, 1644, 1575, 1522, 1447, 1433, 1373, 1365, 1274, 1067, 974 cm$^{-1}$. After discharging the material, no cluster stuck on the blade in the dryer was observed, and no cake was detected in the powder.

There are, of course, many alternative embodiments and modifications of the invention which are intended to be included within the following claims.

What is claimed is:

1. An improved process for the production of the modified zinc acrylate fine powder, comprising steps of:
   (a) Stirring under heating zinc oxide and fatty acid in a liquid medium, adding acrylic acid at a temperature of 40 to 75° C.;

(b) Adding 0.02 to 1.0% by weight of nonionic surfactant in the reaction mixture containing zinc acrylate in step (a) and stirring to form a homogeneous cream; and
(c) Removing organic liquid medium and water by distillation under reduced pressure, and pulverizing to afford the zinc acrylate fine powder.

2. The process according to claim 1, wherein said fatty acid is stearic acid or palmitic acid.

3. The process according to claim 1, wherein said organic liquid medium is benzene, toluene or xylene.

4. The process according to claim 1, wherein said nonionic surfactant polyoxyethylene alkyl ethers having a HLB value in the range of 8 to 17.

* * * * *